US008192655B2

(12) United States Patent
Han et al.

(10) Patent No.: US 8,192,655 B2
(45) Date of Patent: Jun. 5, 2012

(54) METHOD OF PREPARING COVERED POROUS BIODEGRADABLE POLYMER MICROSPHERES FOR SUSTAINED-RELEASE DRUG DELIVERY AND TISSUE REGENERATION

(75) Inventors: Dong Keun Han, Seoul (KR); Kwideok Park, Seoul (KR); Jae-Jin Kim, Seoul (KR); Jun Sik Son, Seoul (KR); Soon Eon Bae, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 755 days.

(21) Appl. No.: 12/255,163

(22) Filed: Oct. 21, 2008

(65) Prior Publication Data
US 2009/0317478 A1 Dec. 24, 2009

(30) Foreign Application Priority Data
Jun. 19, 2008 (KR) .................. 10-2008-0058006

(51) Int. Cl.
*B29B 9/00* (2006.01)
(52) U.S. Cl. .................... 264/5; 424/490; 424/497
(58) Field of Classification Search .................. None
See application file for complete search history.

(56) References Cited

U.S. PATENT DOCUMENTS

| 4,652,441 | A | * | 3/1987 | Okada et al. .................. 424/497 |
| 4,675,189 | A | | 6/1987 | Kent et al. |
| 5,019,400 | A | | 5/1991 | Gombotz et al. |
| 5,100,699 | A | | 3/1992 | Roeser |
| 6,506,410 | B1 | | 1/2003 | Park et al. |
| 6,562,374 | B1 | * | 5/2003 | Han et al. ...................... 424/484 |
| 6,709,650 | B1 | | 3/2004 | Sutton et al. |
| 7,842,305 | B2 | * | 11/2010 | Han et al. ...................... 424/426 |
| 2007/0071790 | A1 | * | 3/2007 | Ameer et al. .................. 424/423 |
| 2007/0264341 | A1 | * | 11/2007 | Lee et al. ...................... 424/486 |
| 2009/0148497 | A1 | * | 6/2009 | Ambrose et al. ............... 424/426 |

FOREIGN PATENT DOCUMENTS

| KR | 10-0372751 | 2/2003 |
| KR | 10-0392501 | 7/2003 |
| KR | 10-0760511 | 10/2007 |
| WO | WO 00/55300 A1 | 9/2000 |

OTHER PUBLICATIONS

Taek Kyoung Kim, et al., "Gas Foamed Open Porous Biodegradable Polymeric Microspheres", Biomaterials 27, 2006, pp. 152-159.
Yi Hong, et al., "Preparation of Porous Polylactide Microspheres by Emulsion-Solvent Evaporation Based on Solution Induced Phase Separation", Polymers for Advanced Technologies, 16, 2005, pp. 622-627.

* cited by examiner

*Primary Examiner* — Mary F Theisen
(74) *Attorney, Agent, or Firm* — Ladas & Parry LLP

(57) ABSTRACT

The present invention relates to covered porous biodegradable polymer microspheres for sustained-release drug delivery and tissue regeneration which has an interconnected inner open pore structure having a wide surface area and high porosity and an outer closed pore structure in which the surface of the microsphere is covered with a thin layer of a biodegradable polymer, and thereby the pores formed on the surface and exposed to the outside are closed; and methods for preparing the same. Due to such a characteristic pore structure, the covered porous biodegradable polymer microspheres according to the present invention can prevent the biologically active material from being excessively released in the early stage immediately after administration, and after that, can gradually release the biologically active material through the interconnected inner pore structure over a prolonged period as the biodegradable polymer thin layer is degraded. Therefore, the microsphere of the present invention can be effectively used for sustained-release drug delivery and tissue regeneration.

19 Claims, 3 Drawing Sheets

Prior Art

METHOD OF PREPARING COVERED POROUS BIODEGRADABLE POLYMER MICROSPHERES FOR SUSTAINED-RELEASE DRUG DELIVERY AND TISSUE REGENERATION

The present application claims priority from Korean Patent Application No. 10-2008-58006, filed Jun. 19, 2008, the subject matter of which is incorporated herein by reference in its entirety.

FIELD OF THE INVENTION

The present invention relates to a simple, efficient, and eco-friendly method of preparing a covered porous biodegradable polymer microsphere by using a hydrogen peroxide-containing compound as an effervescent (foaming) agent, where the inside of the microsphere has an interconnected open pore structure having a wide surface area and high porosity and its outer surface has a closed pore structure covered with a thin layer of a biodegradable polymer whereby the pores exposed to the outside are closed, and covered porous biodegradable polymer microspheres prepared by such method which can be effectively used for sustained-release drug delivery and tissue regeneration.

BACKGROUND OF THE INVENTION

In order to use a microsphere as a drug delivery system, it is important to design a formulation so as to maximize the therapeutic efficacy of a drug, enhance a patient's compliance against the drug and minimize the side effects thereof by efficiently delivering the drug to a target site to be treated. In particular, a microsphere for drug delivery using a biodegradable polymer should have the capability of introducing a lipid-soluble or a water-soluble biologically active material as a drug thereinto and the physical property capable of holding and maintaining the drug for a certain period of time within the body. Further, such a microsphere should satisfy a number of criteria for successful use as a drug delivery system, e.g., the stability of being degraded into harmless materials to a human body and the durability that it does not release the drug in early stage immediately after administration and, after being delivered to a target site, can sufficiently release the drug for a desirable period. Since the microsphere has a small particle size of 1 to 500 μm, it can be easily administered to a human body by using a conventional syringe. Further, it has the advantage of maintaining the therapeutic efficacy of a drug for a relatively long period of time with only a single administration. Thus, research on microspheres for drug delivery has been actively underway, but microspheres which satisfy properties, such as effective drug encapsulation, initial drug release (burst) control, homogeneous size distribution and the like, have still not been found.

Biodegradable polymers widely used in the art include polyglycolic acid (PGA), polylactic acid (PLA), lactic acid-glycolic acid copolymer (PLGA), poly-ε-caprolactone (PCL), lactic acid-ε-caprolactone copolymer (PLCL), polydioxanone (PDO), polytrimethylene carbonate (PTMC), poly (amino acid), polyanhydride, polyorthoester and copolymers thereof. However, only PGA, PLA, and PLGA have been approved by the FDA as biodegradable polymers available for use in human body, and used as drug delivery microspheres and porous polymer scaffolds for tissue regeneration.

There are several known methods for preparing microspheres by using such a biodegradable polymer, for example, a solvent evaporation-drying method (U.S. Pat. No. 4,652,441), a phase-separation method (U.S. Pat. No. 4,675,189), a spray-drying method (U.S. Pat. No. 6,709,650), a low temperature solvent extraction method (U.S. Pat. No. 5,019,400) and the like. Recently, a method of improving biocompatibility and drug encapsulation efficiency of a microsphere by using a water-soluble organic solvent, such as acetic acid, lactic acid, acetone and the like instead of dichloromethane or chloroform, for dissolving a biodegradable polymer has been reported (U.S. Pat. No. 5,100,699). However, the above methods are problematic in that they can only prepare nonporous microspheres, that they are very complicated and time-consuming, and that the prepared nonporous microspheres release drugs at a very low speed.

As for methods of preparing porous microspheres, the salt infusion/gas foaming method and the phase-separation method using a solvent/non-solvent combination are known. The former is a method of providing a microsphere with porosity by using an effervescent agent such as ammonium bicarbonate ($NH_4HCO_3$) (Kim et al., Biomaterials 27: 152-159, 2006), and the latter is a method of providing a microsphere with porosity by using a non-solvent material which is miscible with a solvent used for dissolving a polymer but is immiscible with the polymer (Hong et al., Polym. Adv. Technol. 16: 622-627, 2005). Thus prepared porous microspheres are intended to be used as a cell scaffold for tissue regeneration. So, if they are used for drug delivery, because of the larger surface area due to their high porosity, they may be problematic in that the drug encapsulated in the porous microsphere may be entirely released in the early stage immediately after administration, limiting their use for drug delivery.

Meanwhile, hydrogen peroxide ($H_2O_2$) is a safe, effective, powerful and versatile oxidant. Hydrogen peroxide dissolves well in water, ethanol, ether, and the like and is easily degraded into oxygen and water via a catalytic reaction of inorganic materials, such as alkali metals, heavy metals and manganese dioxide, and enzymes such as catalase, and is thus known as an eco-friendly compound. Hydrogen peroxide has been used for a wide variety of industrial applications, such as disinfectants, antiseptics, the bleaching and disinfection of pulps, papers and foods, teeth whitening, agriculture, pollution treatment, propellents of a rocket, and the like. However, there have been no reports on the use of hydrogen peroxide for providing a polymer microsphere with porosity.

The present inventors have therefore studied to prepare biodegradable polymer microspheres which have the advantages of both porous and nonporous microspheres, and found that if a hydrogen peroxide-containing compound is used as an effervescent (foaming) agent for the preparation of a biodegradable polymer microsphere, it is possible to prepare a covered porous biodegradable polymer microsphere that has an interconnected inner open pore structure having a wide surface area and high porosity and an outer closed pore structure in which the surface of the microsphere is covered with a thin layer of a biodegradable polymer, whereby the pores exposed to the outside are closed. The covered porous biodegradable polymer microsphere according to the present invention can effectively control the release of biologically active materials in the early stage immediately after administration, and after that, gradually release the same over a prolonged period as the biodegradable polymer thin film covered on the surface is degraded within the body.

SUMMARY OF THE INVENTION

The primary objective of the present invention is to provide a method of preparing a covered porous biodegradable polymer microsphere useful as a sustained-release drug delivery system and a scaffold for tissue regeneration.

Another objective of the present invention is to provide a method of preparing a covered porous biodegradable polymer microsphere, which can easily regulate the pore size of a microsphere, solve the problems of harmful substances being released and remaining within the body, and improve the sustained-release effect and durability of a drug encapsulated therein.

Still another objective of the present invention is to provide a simple, efficient and eco-friendly method of preparing a covered porous biodegradable polymer microsphere which has an interconnected inner open pore structure having a wide surface area and high porosity and an outer closed pore structure in which the surface of the microsphere is covered with a thin layer of a biodegradable polymer, whereby the pores exposed to the outside are closed.

In accordance with one embodiment of the present invention, a method of preparing a covered porous biodegradable polymer microsphere is provided, which comprises the following steps of:
1) dissolving or dispersing a biologically active material in a polymer solution in which a biodegradable polymer is dissolved in an organic solvent, to prepare a biologically active material-containing polymer solution;
2) adding a hydrogen peroxide-containing compound to the resulting polymer solution and homogeneously mixing them, to prepare a water-in-oil (W/O) emulsion;
3) demulsifying the water-in-oil emulsion with an emulsion stabilizer solution to prepare an oil-in-water (O/W) emulsion; and
4) adding a hydrogen peroxide-degrading catalyst to the oil-in-water emulsion, to evaporate the organic solvent while degrading the hydrogen peroxide.

In accordance with another embodiment of the present invention, a covered porous biodegradable polymer microsphere useful for a sustained-release drug delivery system and a scaffold for tissue regeneration prepared according to the above method are provided.

BRIEF DESCRIPTION OF THE DRAWINGS

The embodiments of the present invention will be described in detail with reference to the following drawings.

DETAILED DESCRIPTION OF THE INVENTION

Figure 1A:
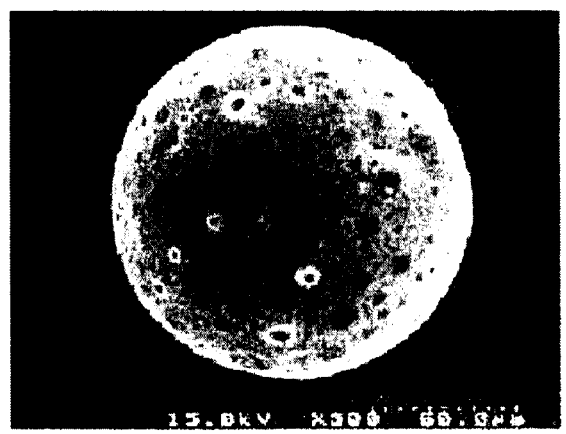
FIGS. 1A and 1B are scanning electron microscope (SEM) photographs of the surface and cross-section of a covered porous biodegradable polymer microsphere containing a biologically active material prepared according to the method of the present invention, respectively.

The term "covered porous biodegradable polymer microsphere" used herein means that an interconnected pore structure having a large surface area and high porosity is formed inside a microsphere, while the outer surface of a microsphere has a closed pore structure covered with a biodegradable polymer in the form of a thin film, which results in the closure of the pores formed on the surface and exposed to the outside. Because the pores formed on the surface of a microsphere are exposed to the outside and have an open structure, there have been problems where the biologically active material encapsulated in the microsphere would be entirely released from the microsphere through the interconnected pore structure in the early stage immediately after administration. The "covered" porous structure of the microsphere in accordance with the present invention solves the above-mentioned problem. Because the biodegradable polymer thin film covering the surface of the microsphere closes the pores formed on the surface and exposed to the outside, the microsphere of the present invention can effectively control the release of a biologically active material in the early stage immediately after the administration and gradually release the same for a prolonged period as the biodegradable polymer thin film covering the surface is degraded within the body after the microsphere is successfully delivered to the target site to be treated.

Hereinafter, the present invention is described in more detail.

The method of preparing a covered porous biodegradable polymer microsphere according to the present invention comprises:
1) dissolving or dispersing a biologically active material in a polymer solution in which a biodegradable polymer is dissolved in an organic solvent, to prepare a biologically active material-containing polymer solution;
2) adding a hydrogen peroxide-containing compound to the resulting polymer solution and homogeneously mixing them, to prepare a water-in-oil (W/O) emulsion;
3) demulsifying the water-in-oil emulsion with an emulsion stabilizer solution to prepare an oil-in-water (O/W) emulsion; and
4) adding a hydrogen peroxide-degrading catalyst to the oil-in-water emulsion, to evaporate the organic solvent while degrading the hydrogen peroxide.

Step 1) above is for preparing a polymer solution containing a biologically active material by dissolving or dispersing a biodegradable polymer and a biologically active material in an organic solvent capable of dissolving the biodegradable polymer.

Suitable biodegradable polymers for the present invention can be of any kind, so long as they are not toxic for human beings and can be degraded in vivo, and may include, but are not limited to, polyglycolic acid (PGA), polylactic acid (PLA), lactic acid-glycolic acid (PLGA) copolymer, poly-ε-caprolactone (PCL), poly(amino acid), polyanhydride, polyorthoester, derivatives and copolymers thereof. Among them, it is desirable to use polylactic acid (PLA), polyglycolic acid (PGA), lactic acid-glycolic acid (PLGA) copolymer and mixtures thereof that have been approved by the FDA as biodegradable polymers useable for human beings. Specifically, the above biodegradable polymer has a weight-average molecular weight ranging from about 5,000 g/mol to about 2,000,000 g/mol, more specifically, about 10,000 g/mol to about 700,000 g/mol, but is not limited thereto.

The type of organic solvent used for dissolving the above biodegradable polymer may vary according to the type of the polymer used and may include methylene chloride, chloroform, carbon tetrachloride, acetone, dioxane, tetrahydrofuran, hexafluoroisopropanol and the like. It is desirable to use methylene chloride and chloroform. The biologically active material-containing polymer solution can be prepared by dissolving the biodegradable polymer and biologically active material in such an organic solvent at the same time. Alternatively, it can be prepared by dissolving the biodegradable polymer in the organic solvent in advance, and then dispersing the biologically active material therein. The biodegradable polymer can be used in the amount of about 5 wt % to about 15 wt % based on the weight of the organic solvent, and the biologically active material can be used in the amount of about 0.1 wt % to about 50 wt % based on the weight of the biodegradable polymer.

Suitable biologically active materials for the present invention may include growth factors, growth hormones, peptide or protein drugs, antiinflammatory drugs, anticancer agents, antiviral agents, sex hormones, antibiotics, antimicrobial agents and compounds. Representative examples thereof may include growth factors such as transforming growth factor (TGF), fibroblast growth factor (FGF), bone morphogenic protein (BMP), vascular endothelial growth factor (VEGF), epidermal growth factor (EGF), insulin-like growth factor (IGF), platelet-derived growth factor (PDGF), nerve growth factor (NGF), hepatocyte growth factor (HGF), placental growth factor (PlGF), granulocyte colony stimulating factor (G-CSF) and the like; peptide or protein drugs such as heparin, animal growth hormones, human growth hormones (hGH), erythropoietin (EPO), interferon (INF), follicle-stimulating hormone (FSH), luteinizing hormone (LH), goserelin acetate, luteinizing hormone-releasing hormone (LH-RH) agonist of decapeptyl and the like; antiinflammatory drugs such as dexamethasone, indomethacin, ibuprofen, ketoprofen, piroxicam, flurbiprofen, diclofenac and the like; anticancer agents such as paclitaxel, doxorubicin, carboplatin, camptothecin, 5-fluorouracil, cisplatin, cytosine arabinoside, methotrexate and the like; antiviral agents such as acyclovir, ganciclovir, cidofivir, entecavir and the like; sex hormones such as testosterone, estrogen, progesterone, estradiol and the like; antibiotics such as tetracycline, minocycline, doxycycline, ofloxacin, levofloxacin, ciprofloxacin, clarithromycin, erythromycin, cefaclor, cefotaxime, imipenem, penicillin, gentamicin, streptomycin, vancomycin and the like; antifungal agents such as ketoconazole, itraconazole, fluconazole, amphotericin-B, griseofulvin and the like; compounds such as β-glycerophosphate, ascobate, hydrocortisone, 5-azacytidine and the like.

Step 2) above is for preparing a water-in-oil (W/O) emulsion (primary emulsion) by adding a hydrogen peroxide-containing compound as an effervescent (foaming) agent to the polymer solution obtained in step 1) and homogeneously mixing them.

The hydrogen peroxide-containing compound added in this step functions to form an interconnected pore structure having a wide surface area and high porosity inside the microsphere, and at the same time, cover the surface of the microsphere with a biodegradable polymer thin film, resulting in the closure of the pores formed on the surface and exposed to the outside.

In the conventional porous microspheres, the pores formed on the surface are open and exposed to the outside and thus have a problem in that the biologically active material encapsulated within the pores of the microsphere are easily released through the interconnected pore structure in the early stage immediately after administration. However, the present invention solves such a problem by using a hydrogen peroxide-containing compound as an effervescent (foaming) agent, which functions to form numerous pores inside the microsphere and cover the exposed pores formed on the surface thereof with a biodegradable polymer thin film.

Further, due to the use of the hydrogen peroxide-containing compound, the present invention has several advantages: it is possible to regulate the pore size and porosity of a microsphere easily; it is possible to produce an eco-friendly microsphere since the degradation of hydrogen peroxide generates only oxygen and water; and it is possible to maximize the formation of a pore structure by the above generated oxygen bubbles and expect a strong disinfection effect on the polymer scaffold, leading to a remarkable increase in microsphere biocompatibility.

The hydrogen peroxide-containing compound of step 2) is used in an amount of about 1 vol % to about 100 vol %, or about 10 vol % to about 80 vol % based on the volume of the polymer solution. Suitable hydrogen peroxide-containing compounds for the present invention are a liquid or a solid material containing pure hydrogen peroxide in the amount of about 1 vol % to about 50 vol %, and may include hydrogen peroxide aqueous solutions, urea hydrogen peroxide (carbamide peroxide), sodium percarbonate (sodium carbonate hydrogen peroxide), solid hydrogen peroxide which is prepared by freeze-drying hydrogen peroxide at a low temperature, effervescent compounds in which hydrogen peroxide binds to an organic or an inorganic compound, and mixtures thereof. Specifically, a hydrogen peroxide aqueous solution containing pure hydrogen peroxide in the amount of about 3 vol % to about 50 vol % may be used.

The resulting polymer mixture obtained in step 2) is a water-in-oil (W/O) emulsion in which the aqueous phase is a discontinuous phase and the oleic phase is a continuous phase. The preparation of such an emulsion is carried out, without limitation, by vigorously stirring the mixture for a certain period of time. For example, a hydrogen peroxide-containing compound may be added to the biologically active material-containing polymer solution, followed by stirring at a rate of about 10 rpm to about 100 rpm for about 1 sec to about 10 min, to thereby obtain a water-in-oil emulsion where the aqueous solution containing the hydrogen peroxide-containing compound is encapsulated within the biodegradable polymer microsphere.

Step 3) above is for preparing an oil-in-water (O/W) emulsion by demulsifying the water-in-oil emulsion obtained in step 2) with an emulsion stabilizer solution. In some embodiments, while the emulsion stabilizer solution is stirred at a temperature of about 10° C. to 80° C. and at a rate of about 50 rpm to 10,000 rpm, the water-in-oil emulsion is slowly added thereto, leading to demulsification. As such, an oil-in-water (O/W) emulsion in which the aqueous phase is a continuous phase and the oleic phase is a discontinuous phase is obtained.

Any type of emulsion stabilizer may be used in the present invention, as long as it is nontoxic to human beings and the environment, is miscible with water while immiscible with an organic solvent, and can improve stability of an emulsion. Examples of emulsion stabilizers may include water-soluble synthetic polymers such as polyvinyl alcohol (PVA), polyvinyl pyrrolidone, polyethylene glycol, poloxamer and the like; and cellulose derivatives such as hydroxypropyl cellulose, hydroxypropyl methylcellulose and the like. The above emulsion stabilizer may be used in an amount of about 0.1 wt % to about 20 wt % based on the weight of the water-in-oil emulsion.

Step 4) above is for evaporating the organic solvent while degrading hydrogen peroxide by adding a hydrogen peroxide-degrading catalyst to the oil-in-water emulsion obtained in step 3). In order to degrade the hydrogen peroxide-containing compound encapsulated within the biodegradable polymer microsphere which is demulsified in the form of an oil-in-water emulsion in step 3), a hydrogen peroxide-degrading catalyst is added thereto, followed by stirring at a rate of about 10 rpm to about 100 rpm for 5 min to 4 hr. As such, the organic solvent is evaporated while the hydrogen peroxide is degraded, to thereby obtain a covered porous biodegradable polymer microsphere having a characteristic pore structure.

Suitable hydrogen peroxide-degrading catalysts useful for degradation of the hydrogen peroxide-containing compound may include enzymatic catalysts such as catalase; inorganic catalysts such as potassium permangnate, manganese dioxide, potassium iodide, potassium dichromate, sodium carbonate, copper oxide, carbon powder and the like; and physical catalysts such as electricity, heat, ultraviolet (UV) light and the like. In one embodiment, catalase is used as a hydrogen peroxide-degrading catalyst. The hydrogen peroxide-degrading catalyst may be used in an amount of about 0.01 vol % to 10 vol % based of the volume of the oil-in-water emulsion.

The above prepared microspheres may be easily collected by centrifugation, washed several times to completely remove impurities, freeze-dried, and then, stored in a particle form.

With respect to the method of preparing the covered porous biodegradable polymer microsphere according to the present invention, pores formed on the microsphere have a mostly circular shape, a porosity of about 5% to about 98% and a pore size of about 0.1 μm to about 50 μm, and their distribution and size are proportional to the amount of the hydrogen peroxide-containing compound used as an effervescent (foaming) agent. Further, since the method of the present invention generates only water and oxygen during the degradation of hydrogen peroxide, it can prepare a microsphere in an eco-friendly manner; and it is possible to maximize the formation of a pore structure by the above generated oxygen bubbles and expect a strong disinfection effect on the polymer scaffold.

The covered porous biodegradable polymer microsphere prepared according to the method of the present invention may have a particle size of about 1 μm to about 500 μm, or about 50 μm to about 300 μm. The particle size may be determined depending on the viscosity of the polymer solution, stirring rate, viscosity of the emulsion stabilizer, the volume ratio of the hydrogen peroxide-containing aqueous solution, and the like.

The covered porous biodegradable polymer microsphere in accordance with the present invention is a novel microsphere having a characteristic structure totally different from the previously known microspheres. In particular, the outer surface of the microsphere has a closed pore structure covered with a biodegradable polymer thin film, which acts to control the initial release (burst) of a drug encapsulated within the pores after administration. Meanwhile, the inside of the microsphere has an interconnected open pore structure having a wide surface area and high porosity, which makes it possible to gradually release the drug over a prolonged period as the biodegradable polymer thin film is degraded within the body. Therefore, the covered porous biodegradable polymer microsphere of the present invention can be effectively used as a sustained-release drug delivery system and a scaffold for tissue regeneration.

EXAMPLES

Embodiments of the present invention will now be described in more detail with reference to the following examples. However, the following examples are provided for the purpose of illustration and are not to be construed as limiting the scope of the invention.

Example 1

A lactic acid-glycolic acid copolymer (PLGA, IV: 0.16-0.24 dl/g) (500 mg) containing lactic acid and glycolic acid in a weight ratio of 50:50 was dissolved in 6 ml of methylene chloride. To the resulting solution was added 5 ml of a 30% hydrogen peroxide aquous solution, and then the mixture was stirred at 5,000 rpm for 3 min by means of a homogenizer, to thereby obtain a primary water-in-oil (W/O) emulsion. As an emulsion stabilizer, 300 ml of a 0.2% polyvinyl alcohol (PVA) solution was prepared and stirred at 70 rpm at 40° C. While stirring the emulsion stabilizer solution, the primary water-in-oil emulsion was added thereto, to obtain an oil-in-water (O/W) emulsion. When the emulsion was stabilized, catalase was added as a hydrogen peroxide-degrading catalyst and stirred at 70 rpm for 4 hr, resulting in a degradation of the hydrogen peroxide encapsulated within the microsphere simultaneously with the evaporation of methylene chloride. The above prepared microspheres were collected by centrifugation, washed with distilled water several times to remove impurities and subjected to freeze-drying, to thereby obtain covered porous biodegradable PLGA microspheres.

Figure 1B:
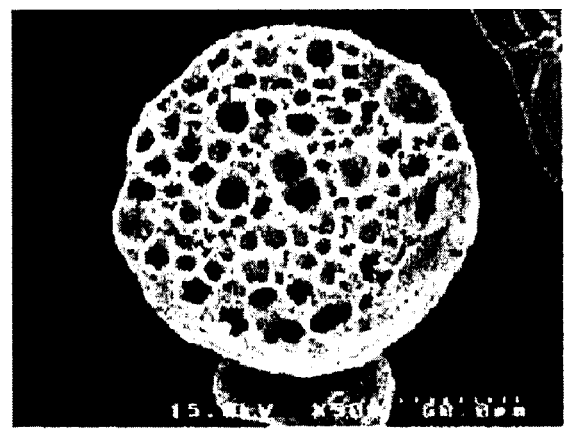

The surfaces and cross-sections of the covered porous biodegradable PLGA microspheres prepared above were observed using a scanning electron microscope (SEM). As shown in FIGS. 1A and 1B, it was found that, while the inside of the microsphere had a maximized porous structure, its surface was covered with a thin film, and thus the pore cavities exposed to the outside were closed. The microspheres were approximately 100 μm in size and had a pore size of 1 to 30 μm and a porosity of 95%. Further, in order to examine the thin film covering the surface of the microspheres, $^1$H-NMR, FT-IR, GPC and DSC analyses were conducted, where it was confirmed that the surface of the microspheres was covered with PLGA used as a biodegradable polymer.

Example 2

The covered porous biodegradable PLGA microspheres in which dexamethasone is encapsulated were prepared according to the same method as described in Example 1 except that acetone was used as the organic solvent instead of methylene chloride, and 10 mg of dexamethasone was added as a biologically active material when the primary water-in-oil emulsion was prepared.

Thus prepared covered porous biodegradable PLGA microspheres showed a pore structure, size and distribution similar to those of Example 1.

Example 3

The covered porous biodegradable PLGA microspheres were prepared according to the same method as described in Example 1 except that 500 mg of lactic acid-glycolic acid copolymer (PLGA, IV: 0.16-0.24 dl/g) containing lactic acid and glycolic acid in a weight ratio of 72:25 was dissolved in 12 ml of chloroform, and then 6 ml of a 40% urea hydrogen peroxide aquous solution was added, followed by the addition of 10 μg of transforming growth factor (TGF), to thereby prepare a primary water-in-oil emulsion, and that potassium permanganate, instead of catalase, was used as a catalyst.

Thus prepared covered porous biodegradable PLGA microspheres showed a pore structure, size and distribution similar to those of Example 1.

Example 4

The covered porous biodegradable PLGA microspheres were prepared according to the same method as described in Example 1 except that 500 mg of lactic acid-glycolic acid copolymer (PLGA, IV: 1.3-1.7 dl/g) containing lactic acid and glycolic acid in a weight ratio of 85:15 was dissolved in 8 ml of methylene chloride, and then 5 ml of a 50% sodium percabonate aquous solution was added, followed by the addition of 10 ng of bone morphogenic protein (BMP), to prepare a primary water-in-oil emulsion, and manganese dioxide, instead of catalase, was used as a catalyst.

Thus prepared covered porous biodegradable PLGA microspheres showed a pore structure, size and distribution similar to those of Example 1.

Example 5

The covered porous biodegradable PLA microspheres were prepared according to the same method as described in Example 1 except that 500 mg of poly lactic acid (PLA, IV: 0.16-0.24 dl/g) was dissolved in 10 ml of methylene chloride, and then 5 ml of a 50% solid hydrogen peroxide aquous solution was added, followed by the addition of 10 μg of fibroblast growth factor (FGF), to thereby prepare a primary water-in-oil emulsion, and copper oxide, instead of catalase, was used as a catalyst.

Thus prepared covered porous biodegradable PLA microspheres were approximately 300 μm in size and had a pore size of 5 to 40 μm and a porosity of 90%. Further, in order to examine the thin film covering the surface of the microspheres, $^1$H-NMR, FT-IR, GPC and DSC analyses were conducted, where it was confirmed that the surface of the microspheres was covered with PLGA used as a biodegradable polymer.

Example 6

The covered porous biodegradable PCL microspheres were prepared according to the same method as described in Example 1 except that 500 mg of poly-$\epsilon$-caprolactone (PCL, IV: 1.3-1.8 dl/g) was dissolved in 10 ml of methylene chloride, and then 10 ml of a 30% hydrogen peroxide aqueous solution was added, followed by the addition of 10 μg of epidermal growth factor (EGF), to thereby prepare a primary water-in-oil emulsion, and carbon powders, instead of catalase, were used as a catalyst.

Thus prepared covered porous biodegradable PCL microspheres were approximately 150 μm in size and had a pore size of 3 to 30 μm and a porosity of 80%. Further, in order to examine the thin film covering the surface of the microspheres, $^1$H-NMR, FT-IR, GPC and DSC analyses were conducted, where it was confirmed that the surface of the microsphere was covered with PCL used as a biodegradable polymer.

Example 7

The covered porous biodegradable PLCL microspheres were prepared according to the same method as described in Example 1 except that 500 mg of lactic acid-$\epsilon$-caprolactone copolymer (PLCL, IV: 1.3-1.8 dl/g) containing lactic acid and $\epsilon$-caprolactone in a weight ratio of 70:30 was dissolved in 10 ml of methylene chloride, and then 5 ml of a 50% hydrogen peroxide aqueous solution was added, followed by the addition of 10 μg of vascular endothelial growth factor (VEGF), to prepare a primary water-in-oil emulsion, and ultraviolet (UV), instead of catalase, was used as a catalyst.

Thus prepared covered porous biodegradable PLCL microspheres were approximately 50 μm in size and had a pore size of 1 to 30 μm and a porosity of 98%. Further, in order to examine the thin film covering the surface of the microspheres, $^1$H-NMR, FT-IR, GPC and DSC analyses were conducted, where it was confirmed that the surface of the microsphere was covered with PLCL used as a biodegradable polymer.

Comparative Example 1

The porous biodegradable PLGA microsphere in which dexamethasone is encapsulated therein was prepared according to the same method as described in Example 2 except that 500 mg of lactic acid-glycolic acid copolymer (PLGA, IV: 0.16-0.24 dl/g) containing lactic acid and glycolic acid in a weight ratio of 50:50 was dissolved in 6 ml of methylene chloride, and then 5 ml of a 10% ammonium bicarbonate aqueous solution was added thereto, followed by the addition of 10 mg of dexamethasone, to thereby prepare a primary water-in-oil emulsion.

Figure 2:
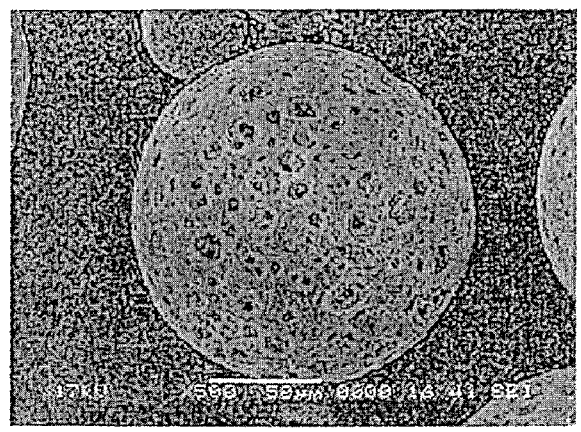
FIG. 2 is a scanning electron microscope (SEM) photograph of the surface of a porous biodegradable polymer microsphere containing a biologically active material prepared according to the conventional method.

The surface of the porous biodegradable PLGA microsphere prepared above was observed with a scanning electron microscope (SEM). As shown in FIG. 2, it was found that the surface of the microsphere was not covered with a thin film and the pores having an open structure were exposed outside.

Comparative Example 2

The nonporous biodegradable PLGA microsphere in which dexamethasone is encapsulated therein was prepared according to the same method as described in Example 2 except that 500 mg of lactic acid-glycolic acid copolymer (PLGA, IV: 0.16-0.24 dl/g) containing lactic acid and glycolic acid in a weight ratio of 50:50 was dissolved in 6 ml of methylene chloride, and then 10 mg of dexamethasone was added, to thereby prepare a primary water-in-oil emulsion.

Figure 3:
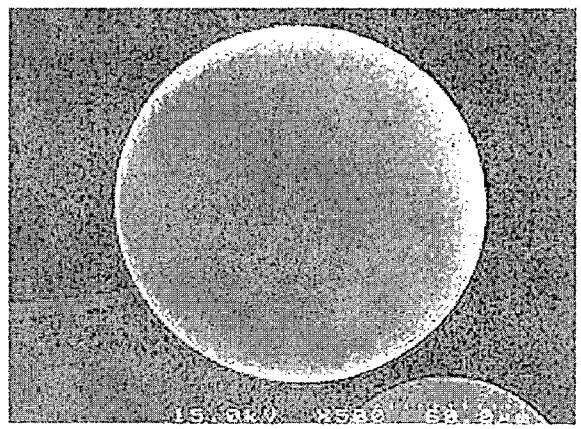
FIG. 3 is a scanning electron microscope (SEM) photograph of the surface of a nonporous biodegradable polymer microsphere containing a biologically active material prepared according to the conventional method.

The surface of the nonporous biodegradable PLGA microsphere prepared above was observed with a scanning electron microscope (SEM). As shown in FIG. 3, it was found that the microsphere was a nonporous structure with no pores inside or at the surface thereof.

Test Example 1

Each of the microspheres (10 mg) prepared in Example 2 and Comparative Examples 1 and 2 was mixed with a phosphate-buffered saline (PBS, pH 7.4), and a specific amount of sample was collected from the resulting PBS solution everyday for 30 days. The collected samples were subjected to UV spectrophotometer analysis at 242 nm to measure the amount of dexamethasone released in the PBS solution from the microsphere.

Figure 4:
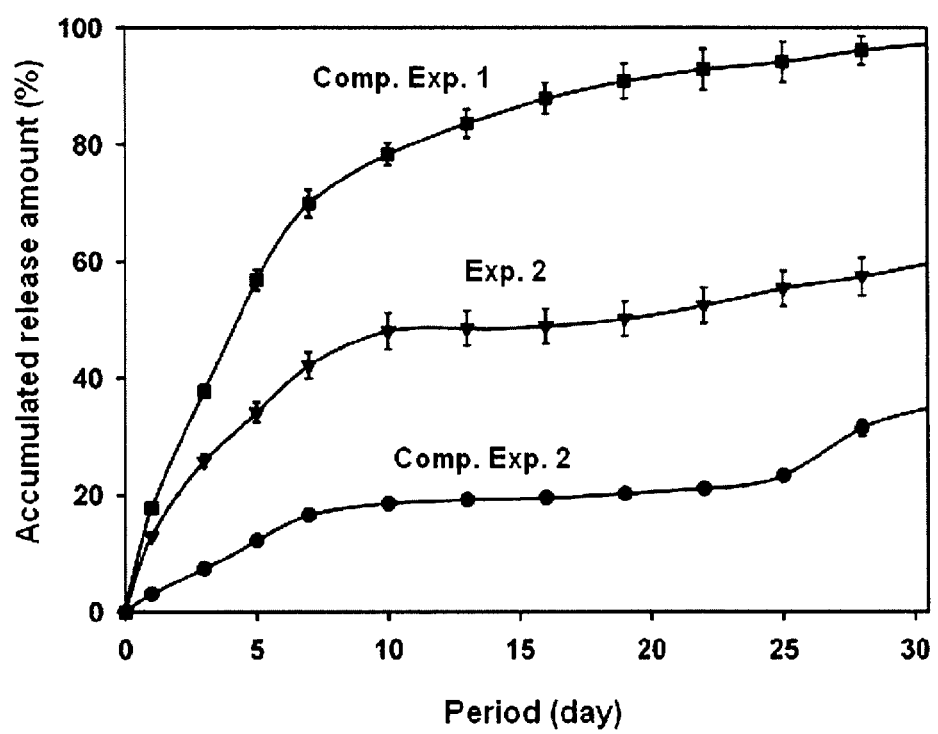
FIG. 4 is a graph showing the in vitro drug-release behavior of dexamethasone from a covered porous biodegradable polymer microsphere prepared according to the method of the present invention.

FIG. 4 is a graph comparing the in vitro drug-releasing behavior of dexamethasone from the covered porous biodegradable polymer microspheres prepared in Example 2 with those prepared in Comparative Examples 1 and 2. As shown in FIG. 4, the release curve of the covered porous biodegradable polymer microsphere prepared according to the method of the present invention was found to exist between the release curves of nonporous and porous microspheres, suggesting that the release of the drug is effectively controlled in the early stage immediately after administration, and after a certain period of time, the drug is gradually released from the microsphere over a prolonged period. These results demonstrate that the covered porous biodegradable polymer microsphere of the present invention can be effectively used as a sustained-release drug delivery system.

While the present invention has been described and illustrated with respect to a preferred embodiment of the invention, it will be apparent to those skilled in the art that variations and modifications are possible without deviating from the broad principles and teachings of the present invention, which should be limited solely by the scope of the claims appended hereto.

What is claimed:

1. A method of preparing a covered porous biodegradable polymer microsphere comprising: dissolving or dispersing a biologically active material in a polymer solution in which a biodegradable polymer is dissolved in an organic solvent, to prepare a biologically active material-containing polymer solution; adding a hydrogen peroxide-containing compound to said polymer solution and homogeneously mixing the solution, to prepare a water-in-oil (W/O) emulsion; demulsifying the water-in-oil emulsion with an emulsion stabilizer solution, to prepare an oil-in-water (O/W) emulsion; and adding a hydrogen peroxide-degrading catalyst to the oil-in-water emulsion, to evaporate the organic solvent while degrading hydrogen peroxide.

2. The method according to claim 1, wherein the biodegradable polymer is lactic acid-glycolic acid copolymer (PLGA).

3. The method according to claim 1, wherein the biodegradable polymer has a weight-average molecular weight ranging from about 5,000 g/mol to about 2,000,000 g/mol.

4. The method according to claim 1, wherein the organic solvent is methylene chloride.

5. The method according to claim 1, wherein the biodegradable polymer is used in an amount of about 5 wt % to about 15 wt % based on the weight of the organic solvent.

6. The method according to claim 1, wherein the biologically active material is used in an amount of about 0.1 wt % to about 50 wt % based on the weight of the biodegradable polymer.

7. The method according to claim 1, wherein the biologically active material is dexamethasone.

8. The method according to claim 1, wherein the hydrogen peroxide-containing compound is used in an amount of about 1 vol % to about 100 vol % based on the volume of the polymer solution.

9. The method according to claim 1, wherein the hydrogen peroxide-containing compound is a liquid compound containing pure hydrogen peroxide in an amount of about 1 vol % to about 50 vol %.

10. The method according to claim 9, wherein the hydrogen peroxide-containing compound is hydrogen peroxide aqueous solutions.

11. The method according to claim 1, wherein the water-in-oil emulsion is prepared by adding a hydrogen peroxide-containing compound to the biologically active material-containing polymer solution and stirring the resulting mixture at a rate of about 10 rpm to about 100 rpm for about 1 sec to about 10 min.

12. The method according to claim 1, wherein the oil-in-water emulsion is prepared by gradually demulsifying the water-in-oil emulsion obtained with an emulsion stabilizer solution while stirring the emulsion stabilizer solution in which an emulsion stabilizer is dissolved, at a temperature of about 10° C. to about 80° C. and at a rate of about 50 rpm to about 10,000 rpm.

13. The method according to claim 1, wherein the emulsion stabilizer is polyvinyl alcohol (PVA).

14. The method according to claim 1, wherein the emulsion stabilizer is used in an amount of about 0.1 wt % to about 20 wt % based on the weight of the water-in-oil emulsion.

15. The method according to claim 1, wherein the hydrogen peroxide-degrading catalyst is enzymatic catalysts.

16. The method according to claim 15, wherein the enzymatic catalyst is catalase.

17. The method according to claim 15, wherein the inorganic catalyst is selected from the group consisting of potassium permangnate, manganese dioxide, potassium iodide, potassium dichromate, sodium carbonate, copper oxide and carbon powders.

18. The method according to claim 15, wherein the physical catalyst is electricity, heat, or ultraviolet (UV) light.

19. The method according to claim 1, wherein the hydrogen peroxide-degrading catalyst is used in the amount of about 0.01 vol % to about 10 vol % based on the volume of the oil-in-water emulsion.

* * * * *